(12) United States Patent
Palmer et al.

(10) Patent No.: US 8,585,724 B2
(45) Date of Patent: Nov. 19, 2013

(54) SURGICAL CUTTING INSTRUMENT WITH DISTAL SUCTION CAPABILITY

(75) Inventors: Allen C. Palmer, Arlington, TN (US); John P. Flynn, Collierville, TN (US)

(73) Assignee: Gyrus Ent, L.L.C., Bartlett, TN (US)

( * ) Notice: Subject to any disclaimer, the term of this patent is extended or adjusted under 35 U.S.C. 154(b) by 120 days.

(21) Appl. No.: 13/013,240

(22) Filed: Jan. 25, 2011

(65) Prior Publication Data
US 2012/0191117 A1      Jul. 26, 2012

(51) Int. Cl.
A61B 17/32      (2006.01)

(52) U.S. Cl.
USPC ........................................ 606/170

(58) Field of Classification Search
USPC ......... 606/169, 170, 171, 172, 184, 185, 177, 606/79, 83; 604/22
See application file for complete search history.

(56) References Cited

U.S. PATENT DOCUMENTS

| | | | |
|---|---|---|---|
| 3,882,872 A | | 5/1975 | Douvas et al. |
| 3,937,222 A | | 2/1976 | Banko |
| 4,844,064 A | | 7/1989 | Thimsen et al. |
| 5,112,299 A | | 5/1992 | Pascaloff |
| 5,674,235 A | | 10/1997 | Parisi |
| 5,730,752 A | | 3/1998 | Alden et al. |
| 5,947,983 A | * | 9/1999 | Solar et al. ............. 606/170 |
| 6,342,061 B1 | | 1/2002 | Kauker et al. |
| 6,419,684 B1 | | 7/2002 | Heisler et al. |
| 6,478,805 B1 | * | 11/2002 | Marino et al. .......... 606/170 |
| 6,979,332 B2 | * | 12/2005 | Adams .................... 606/45 |
| 7,247,161 B2 | | 7/2007 | Johnston et al. |
| 7,318,831 B2 | | 1/2008 | Alvarez et al. |
| 2003/0163126 A1 | | 8/2003 | West, Jr. |
| 2005/0070818 A1 | | 3/2005 | Mueller, Jr. |
| 2005/0096649 A1 | | 5/2005 | Adams |
| 2011/0190801 A1 | * | 8/2011 | Mark et al. ............. 606/170 |

FOREIGN PATENT DOCUMENTS

GB      2 042 902 A      10/1980

OTHER PUBLICATIONS

Apr. 12, 2012 International Search Report and Written Opinion issued in Application No. PCT/US2012/020171.
U.S. Appl. No. 13/013,117, filed Jan. 25, 2011.
U.S. Appl. No. 13/029,588, filed Feb. 17, 2011.

* cited by examiner

*Primary Examiner* — Tuan V Nguyen
(74) *Attorney, Agent, or Firm* — Oliff & Berridge, PLC

(57) ABSTRACT

A surgical instrument includes first and second cutting blades, each including a tubular body having proximal and distal ends, with a cutting window disposed at a side of each cutting blade near its distal end. The second cutting blade rotates within the first cutting blade to cut tissue while a vacuum is applied through an internal bore of the second cutting blade. The distal end of each of the cutting blades includes a suction aperture. An area of the first cutting blade suction aperture is smaller than an area of the second cutting blade suction aperture. The instrument is used as a suction tool by applying the vacuum through the internal bore of the second cutting blade while the second cutting blade is stopped from rotating with the cutting windows of the first and second cutting blades misaligned with each other to apply the vacuum through the suction apertures.

26 Claims, 4 Drawing Sheets

SURGICAL CUTTING INSTRUMENT WITH DISTAL SUCTION CAPABILITY

BACKGROUND

This disclosure relates to surgical instruments, and in particular to surgical cutting instruments that use suction, for example, powered shavers, microdebriders and dissector blades.

Surgical apparatus used to shave, cut, resect, abrade and/or remove tissue, bone and/or other bodily materials are known. Such surgical apparatus can include a cutting surface, such as a rotating blade disposed on an elongated inner tube that is rotated within an elongated outer tube having a cutting window. The inner and outer tubes together form a surgical cutting instrument or unit. In general, the elongated outer tube includes a distal end defining an opening or cutting window disposed at a side of the distal end of the outer tube. The cutting window of the outer tube exposes the cutting surface of the inner tube (located at a side of the distal end of the inner tube) to tissue, bone and/or any other bodily materials to be removed. A powered handpiece is used to rotate the inner tube with respect to the outer tube while an outer tube hub (connected to the proximal end of the outer tube) is fixed to the handpiece and an inner tube hub (connected to the proximal end of the inner tube) is loosely held in place by the powered handpiece.

In some instruments the inner tube is hollow and has a cutting window on a side surface of its distal end such that tissue, bone, etc. will be cut or shaved as the cutting window of the inner tube aligns with and then becomes misaligned with the cutting window of the outer tube as the inner tube is rotated within the outer tube. In this regard, it can be said that the cutting device nibbles or takes away small pieces of the bone, tissue, etc. as the inner tube is rotated within the outer tube.

In some instruments a vacuum is applied through the inner tube such that the bodily material that is to be cut, shaved, etc. is drawn into the windows of the inner and outer tubes when those windows become aligned, thereby facilitating the cutting, shaving, etc. of the tissue, which then travels through the inner tube due to the suction. It also is common to supply an irrigation fluid, which can include a liquid, to the surgical site via a passage provided between the inner and outer tubes.

SUMMARY

Many times during surgery, the surgeon wishes to apply suction to the surgical site without performing cutting with the surgical instrument. This usually is done by withdrawing the surgical instrument and inserting a dedicated suction device (for example, a suction wand which is a tube to which suction is applied). However, exchanging the surgical tool for the dedicated suction device is time-consuming. Furthermore, insertion and removal of instruments into the patient can cause trauma and irritation to the passage of the patient, and thus it is desirable to minimize the number of times that surgical instruments need to be withdrawn and inserted/reinserted into the patient.

It is conceivable that the surgeon can use the surgical cutting instrument as a suction device, for example, by stopping rotation of the inner cutting tube while continuing to apply suction through the inner tube. By careful operation of the pedal (or other control device) which controls the rotation of the inner tube, the surgeon can cause the cutting windows of the inner and outer tubes to be aligned with each other such that suction can be applied to the surgical site through the aligned windows of the inner and outer tubes. However, because the windows of the inner and outer tubes are cutting surfaces (and typically include serrations), most surgeons choose not to use the surgical cutting tool as a suctioning device because tissue adjacent to the outer tube window tends to be drawn into the window and partially cut and/or irritated by the cutting surfaces of the inner and outer tubes. Additionally, because the cutting windows of the inner and outer tubes are disposed on a side surface of the distal tips of the inner and outer tubes, the suction is applied from the side of the distal end of the tube, which is not optimal. Most suction wands apply the suction from the very end of the tip such that suction is applied at the very tip of the suction wand.

According to an aspect of the invention, a surgical instrument that performs cutting also can function as a suction wand. This is achieved by providing the surgical instrument with a suction aperture at the distal-most tip of the surgical instrument such that a longitudinal axis of the surgical instrument passes through the suction aperture.

According to some embodiments, the surgical instrument includes a first cutting blade and a second cutting blade. The first cutting blade includes a tubular body having a proximal end and a distal end, with a cutting window disposed at a side of the first cutting blade near the distal end. The second cutting blade includes a tubular body having a proximal end and a distal end, with a cutting window disposed at a side of the second cutting blade near the distal end. The second cutting blade is rotatably disposed inside of the first cutting blade such that the surgical instrument cuts tissue by rotating the second cutting blade within the first cutting blade while a vacuum is applied through an internal bore of the second cutting blade to draw the tissue into the cutting windows of the first and second cutting blades and sever the tissue by rotation of the second cutting blade. The distal end of the first cutting blade includes a first suction aperture through which a longitudinal axis of the first cutting blade extends. Similarly, the distal end of the second cutting blade includes a second suction aperture through which a longitudinal axis of the second cutting blade extends.

The surgical instrument can be used as a suction tool by applying the vacuum through the internal bore of the second cutting blade while the second cutting blade is stopped from rotating with the cutting windows of the first and second cutting blades misaligned with each other so that the vacuum is applied through the first and second suction apertures. When the surgical instrument is used for cutting, most of the suction is applied through the cutting windows because they are located closer to the vacuum source than are the suction apertures (that is, the cutting windows are proximal to the suction apertures). Thus, as the second cutting blade rotates within the first cutting blade, the cutting operation can be performed as usual.

According to some preferred embodiments, a diameter of the first suction aperture is equal to or smaller than a diameter of the second suction aperture. By making the diameter of the second suction aperture, which is on the second (or inner) rotating cutting blade, equal to or larger than the diameter of the first suction aperture on the first (or outer) blade, the suction apertures will not function as a cutting device because tissue will not be pinched (and thus will not be cut) between the two apertures.

The first and second cutting blades preferably are made from a sterilizable material. According to some embodiments, the sterilizable material is a metal such as stainless steel.

According to an aspect of the invention, a surgical method includes inserting the surgical instrument described above into a passage of a patient and then performing a suctioning operation with the surgical instrument. The suctioning operation includes positioning the second cutting blade relative to the first cutting blade so that the cutting windows of the first and second cutting blades are misaligned with each other so that the internal bore of the second cutting blade does not communicate with the passage of the patient through either of the cutting windows of the first and second cutting blades. The method further includes applying a vacuum through the internal bore of the second cutting blade to draw material from the passage of the patient into the internal bore of the second cutting blade through the first and second suction apertures. The first and second cutting blades are not rotated relative to each other during the suctioning operation.

The second cutting blade can be positioned relative to the first cutting blade so that the cutting windows of the first and second cutting blades are misaligned with each other by the surgeon operating the controls of the surgical instrument (for example, by operating a foot pedal) while observing the distal tip of the cutting instrument (for example, with an endoscope as is typically used to observe the surgical procedure) until the cutting window of the inner, second cutting blade is misaligned with the cutting window of the outer, first cutting blade such that the back side of the second cutting blade opposite to the window substantially blocks the window of the first cutting blade.

The method of suctioning can be performed after the surgical instrument has been used for cutting and/or before the surgical instrument has been used for cutting. In either case, it is unnecessary to withdraw the cutting instrument when switching between a cutting operation and a suctioning operation. Furthermore, a separate suction wand may not be needed.

BRIEF DESCRIPTION OF THE DRAWINGS

Various exemplary embodiments of the disclosed surgical tool will be described in detail with reference to the following drawings in which.

DETAILED DESCRIPTION OF EMBODIMENTS

The following exemplary embodiments are described below with reference to the figures in the context of human surgery, such as ear, nose and throat surgery, and in particular sinus surgery as well as head and neck surgery. The following exemplary embodiments may also be utilized in spinal surgery, orthopedic surgery, and various other surgical applications. All exemplary embodiments of the invention are intended to be used in any applicable field of endeavor.

Figure 1:
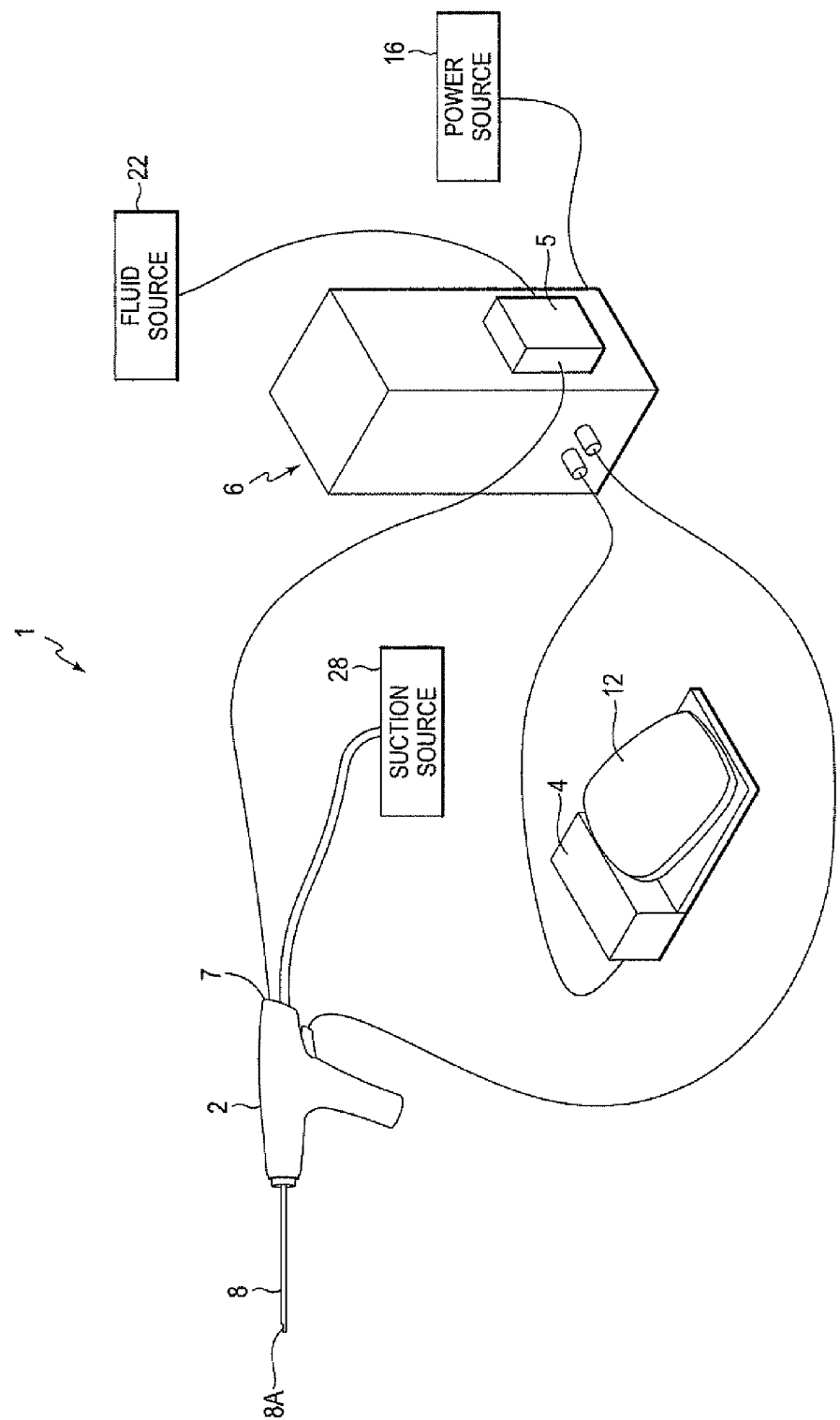
FIG. 1 illustrates a perspective view of a powered surgical tool system that incorporates a surgical instrument, control unit, fluid source and suction source.

FIG. 1 is a schematic of a powered surgical tool system. Except for the tip of the cutting tool, to be described hereafter, the system may be in accordance with the system described in U.S. Pat. No. 7,247,161, the disclosure of which is incorporated herein by reference in its entirety. Another system to which the invention is applicable is described in U.S. Pat. No. 7,318,831, the disclosure of which is incorporated herein by reference in its entirety. As shown in FIG. 1, the powered surgical tool system 1 includes a handle 2, a footswitch 4 (with pedal 12), fluid (liquid and/or gas) source 22, suction source 28, a control unit 6, fluid pump 5 and a fluid inlet/irrigation outlet 7. The system is supplied with power from a power source 16 such as a wall outlet. The suction source 28 may be an external suction source such as provided by attachment to a facility suction outlet provided on a wall. The handle 2 is connected, at its distal end, to a surgical instrument 8. The surgical instrument 8 in this embodiment includes a cutting tip at its distal end 8A that is used, for example, to cut, shave, remove, resect and/or abrade tissue, bone and/or other bodily materials.

Figure 2:
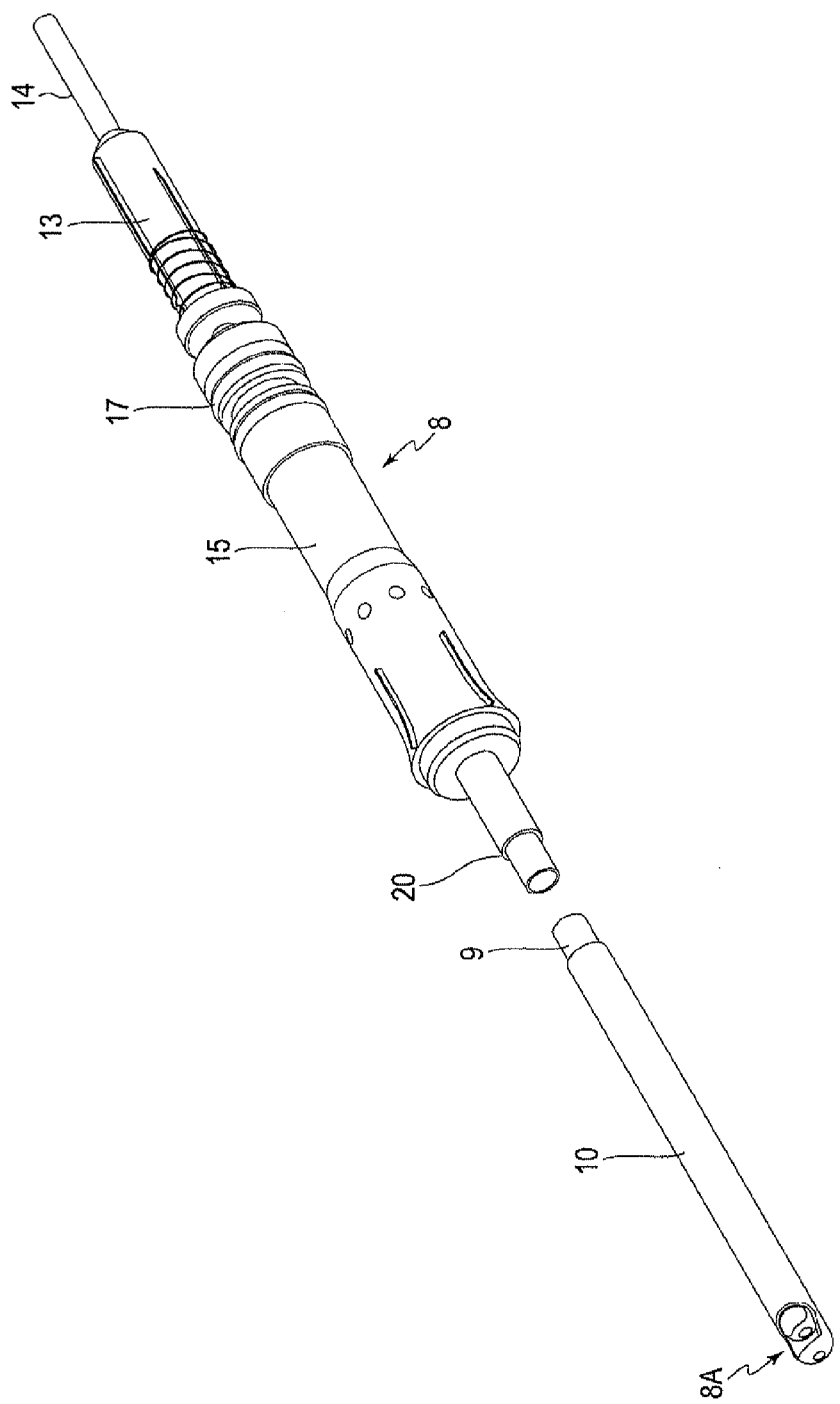
FIG. 2 is a perspective view of an exemplary embodiment of a surgical instrument in accordance with the present disclosure.

FIG. 2 illustrates a perspective view of an exemplary embodiment of the surgical instrument 8 in accordance with aspects of the invention. The instrument 8 incorporates an inner tube 9 and an outer tube 10. In this exemplary embodiment, an inner tube hub 13 is formed on the second end 14 of the inner tube 9 and an outer tube hub 15 is formed on the second end 17 of the outer tube 10. The inner tube 9 is inserted into a fluid passage 20 formed within the outer tube 10 so that the inner tube 9 is co-axially disposed within the outer tube 10 until the external distal tip of the inner tube 9 contacts the internal distal surface of the outer tube 10. The outer tube 10 has a larger diameter than the inner tube 9, thus allowing for insertion of the inner tube 9 within the outer tube 10. However, it should be appreciated that the inner and outer tubes will be pre-assembled prior to delivery to the customer. Thus, a customer will most likely not be inserting the inner tube into the outer tube.

The inner and outer tube hubs 13, 15 couple the inner and outer tubes 9, 10, respectively, to the handle 2. Once coupled to the handle 2, the outer tube 10 will be fixed relative to the handle 2, but the inner tube 9 will be rotatable relative to the outer tube 10 and the handle 2.

Figure 3:
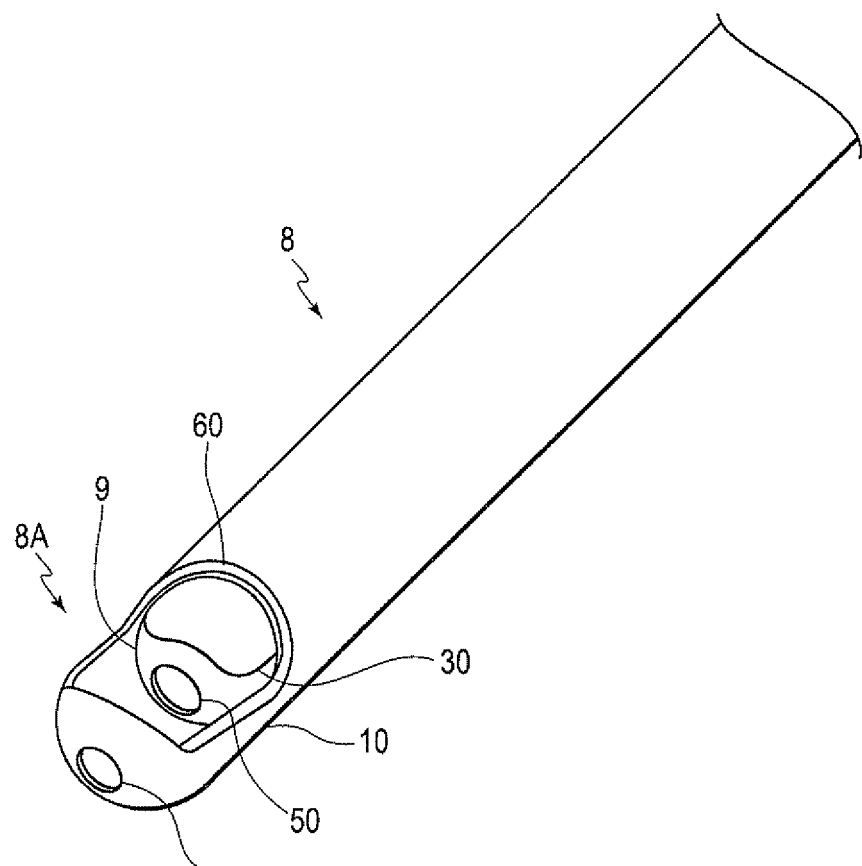
FIG. 3 is a perspective view of a distal tip of a surgical instrument in accordance with the present disclosure, with the inner cutting blade being slightly retracted from its usual position to more clearly show the distal ends of the inner and outer cutting blades.
Figure 4:
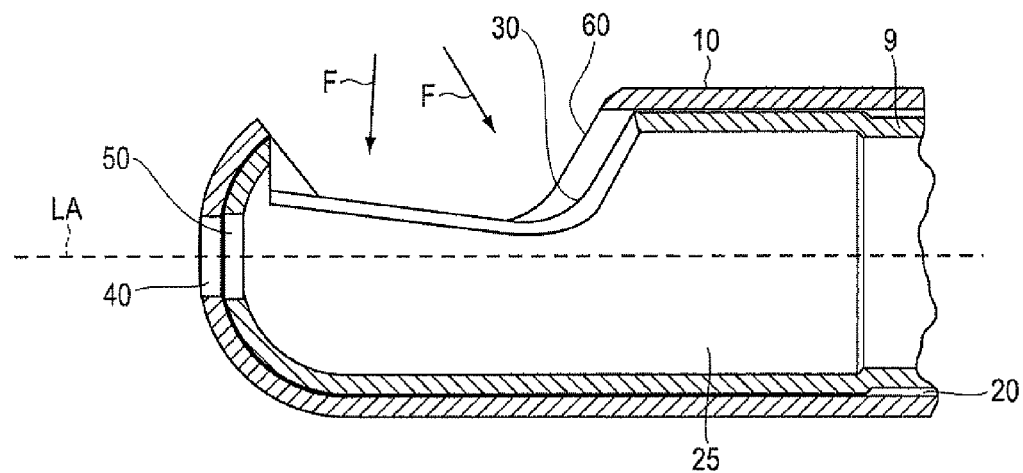
FIG. 4 is a side, cross-sectional view of the FIG. 3 surgical instrument distal tip with the inner cutting blade fully inserted to its usual position and with the cutting windows being in complete alignment.
Figure 5:
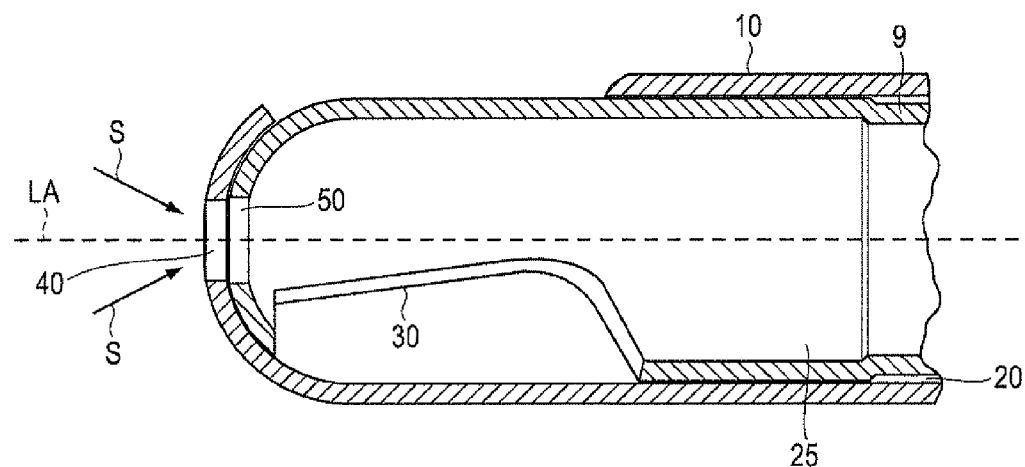
FIG. 5 is a side, cross-sectional view similar to FIG. 4, but with the cutting windows being in complete mis-alignment so that the surgical instrument can be used as a suction device.

FIG. 3 is a perspective view of the distal tip 8a of the surgical instrument 8. FIG. 3 shows the inner tube 9 retracted slightly from its usual position so that the structure of the distal tips of both the inner tube 9 and the outer tube 10 can be more readily seen. The outer tube 10 includes a cutting window 60 disposed at a side of its distal end. Thus, the outer tube 10 also can be referred to as a first cutting blade. The inner tube 9 also includes a cutting window 30 disposed at a side of its distal end. Thus, the inner tube 9 also can be referred to as a second cutting blade. The edges of the cutting windows 30 and 60 can be serrated, smooth or a combination of serrated and smooth to form cutting surfaces. Each of the inner and outer tubes 9, 10 also includes a suction aperture at its distal end as shown even more clearly in FIGS. 4 and 5. As mentioned previously, the inner cutting blade 9 rotates within the outer cutting blade 10, and thus as the inner cutting blade 9 rotates, the cutting windows 30 and 60 become aligned with each other as shown in FIG. 4 and then become misaligned with each other as shown in FIG. 5. When the cutting windows 30 and 60 are misaligned with each other as shown in FIG. 5, the side of the inner tube 9 distal tip opposite from the cutting window 30 blocks the cutting window 60 of the outer cutting blade 10, as will be described in more detail below.

The first, or outer cutting blade 10 thus is a tubular body having a proximal end and a distal end, with a cutting window 60 disposed at a side of the first cutting blade 10 near the distal end. The outer cutting blade 10 also includes a suction aperture 40 at its distal-most end through which a longitudinal axis LA of the outer tube cutting blade 10 extends.

The inner, second cutting blade 9 is a tubular body having a proximal end and a distal end, with cutting window 30 disposed at a side of its distal end. As mentioned previously, the second, inner cutting blade 9 is rotatably disposed inside of the first, outer cutting blade 10 such that the surgical instrument 8 cuts tissue by rotating the second, inner cutting blade 9 within the first, outer cutting blade 10 while a vacuum is applied through an internal bore 25 of the cutting blade 9 to draw the tissue into the cutting windows 30 and 60 of the cutting blades 9 and 10 and sever the tissue by rotation of the cutting blade 9. The inner cutting blade 9 also includes a suction aperture 50 at its distal-most end through which a longitudinal axis LA of the inner tube cutting blade 9 extends.

The surgical instrument 8 can be used as a suction tool by applying the vacuum through the internal bore 25 of the cutting blade 9 while the cutting blade 9 is stopped from rotating and the cutting windows 30 and 60 of the cutting blades 9 and 10 are misaligned with each other as shown in FIG. 5 so that the vacuum is applied through a suction passage defined by the first and second suction apertures 40 and 50. The surgeon operating the instrument 8 can cause the windows 30 and 60 to become oriented in the misaligned state shown in FIG. 5 by, for example, tapping on the pedal 12 that controls the instrument to cause incremental rotation of the inner cutting blade 9 while observing the distal tip of the instrument, for example, by an endoscope, which usually also is disposed at the operating site, until the windows 30 and 60 obtain the state shown in FIG. 5. With the windows 30 and 60 misaligned as shown in FIG. 5, vacuum can be applied through the internal bore 25 of the cutting blade 9 so that the surgical instrument can be used like a suction wand. The flow of fluid toward the suction passage defined by the suction apertures 40 and 50 is illustrated by arrows S in FIG. 5, whereas the flow that occurs during a cutting operation is illustrated by arrows F in FIG. 4.

Although it is not necessary, irrigation fluid also could be supplied through bore 20 when in the state shown in FIG. 5.

When the surgical instrument is used for cutting (that is, when the inner cutting blade 9 is being rotated within the outer cutting blade 10 while irrigation liquid and suction are applied), most of the suction is applied through the cutting windows 30 and 60 because they are located closer to the vacuum source than are the suction apertures 40 and 50 (that is, the cutting windows 30 and 60 are proximal to the suction apertures 40 and 50). Thus, even though the suction apertures 40 and 50 are provided on the distal end of the cutting instrument 8, a cutting operation can be performed in the usual manner (with cutting windows 30 and 60) with substantially no suction being applied through the suction apertures 40 and 50 as the inner cutting blade 9 rotates within the outer cutting blade 10.

During a cutting operation, a small amount of flow will occur through the suction apertures 40 and 50, but this flow does not interfere with the cutting operation. It has been found that the small amount of flow assists in the removal of cut material through the internal bore 25 of the cutting blade during the cutting operation.

It is undesirable for the suction apertures 40 and 50 to function like a cutting element (like the cutting windows 30 and 60). In order to avoid cutting or pinching from occurring when suction is applied through the suction apertures 40 and 50 (including during a cutting operation), it is preferable that the diameter of the suction aperture 40 provided on the outer cutting blade 10 be equal to or smaller than a diameter of the suction aperture 50 provided on the inner cutting blade 9. By making the diameter of the inner suction aperture (aperture 50) on the rotating cutting blade 9 equal to or larger than the diameter of the outer suction aperture (suction aperture 40), the suction apertures 40 and 50 will not function as a cutting device because tissue will not be pinched between the two apertures 40 and 50, or otherwise cut or damaged by those apertures when the instrument is being used as a suction wand and when the instrument is being used as a cutting tool with the inner blade 9 rotating. In the illustrated embodiment, suction aperture 40 is smaller than suction aperture 50.

The edges of the apertures 40 and 50 also can be rounded to further keep them from cutting tissue. However, the apertures do not cut tissue even if they are not rounded.

Another reason that the apertures 40 and 50 do not function to cut tissue is because the apertures 40 and 50 remain aligned with each other even while the inner cutting blade 9 rotates. Due to such alignment, the open suction passage (defined by apertures 40 and 50) exists between the internal bore 25 and an area external of the surgical instrument (that is, an area distal of the surgical instrument tip) through the suction apertures 40 and 50 both when the cutting blade 9 does not rotate and when the cutting blade 9 rotates within the cutting blade 10. In this regard, the suction aperture 50 at the distal end of the inner cutting blade 9 remains in fluid communication with the suction aperture 40 at the distal end of the outer cutting blade 10 as the inner cutting blade 9 rotates, and when it is stationary.

As shown in the embodiment of FIGS. 3-5, the distal ends of the cutting blades 9 and 10 are substantially spherical. As an alternative, the distal ends of the blades 9 and 10 could be flat, with the first and second apertures 40 and 50 being disposed on flat portions of those blades. However, spherical tips are preferred to ease insertion into the patient.

The cutting blades 9 and 10 are made from a sterilizable material. According to some embodiments, the sterilizable material is a metal such as stainless steel.

When the instrument 8 is used for surgery, the surgical instrument 8 is inserted into a passage of a patient. Either before or after (or both before and after) a cutting operation is performed, the surgical instrument 8 can be used to perform a suctioning operation. The suctioning operation includes positioning the inner blade 9 relative to the outer blade 10 so that the cutting windows 30 and 60 are misaligned with each other so that the internal bore 25 of the cutting blade 9 does not communicate with the passage of the patient into which the surgical instrument is inserted through either of the cutting windows 30 and 60. A vacuum applied through the internal bore 25 of the inner cutting blade 9 draws material from the passage of the patient into the internal bore 25 through the suction passage defined by the first and second suction apertures 40 and 50. During performance of the suctioning operation, the inner cutting blade 9 is not rotated relative to outer cutting blade 10.

Thus, it is unnecessary to withdraw the surgical cutting instrument 8 from the patient when switching between a cutting operation and a suctioning operation. Moreover, a separate suctioning wand may not be needed. Thus, the surgical procedure that is performed with the surgical instrument 8 can be performed more quickly and while causing less trauma to the patient.

In the illustrated embodiment, the inner and outer cutting blades 9 and 10 are straight. However, the surgical instrument 8 can have one or more bends in it such that it is not straight.

In such an arrangement, the inner cutting blade 9 would be flexible. Flexible hollow cutting blades are known and used with curved cutting instruments. See, for example, U.S. Pat. No. 4,646,738, the disclosure of which is incorporated herein by reference in its entirety, and see, for example, U.S. Pat. No. 5,707,350, the disclosure of which is incorporated herein by reference in its entirety.

In the illustrated embodiment, the outer cutting blade 10 included an open distal end defined by a suction aperture 40 formed through an otherwise closed portion at the distal tip of the outer cutting blade 10. The invention, however, is not limited to such a structure. For example, the open distal end of the outer cutting blade 10 could be formed by providing an open-ended outer cutting blade 10 (rather than a closed portion having an aperture formed through it). That is, the opening provided at the distal end of the outer cutting blade 10 need not be an aperture that is completely surrounded by wall structure of the outer cutting blade, but instead could be only partially surrounded by wall structure of the outer cutting blade. In addition, the suction aperture 40 does need to be perfectly circular, but could have other shapes.

Another option would be to form the surgical instrument with no suction aperture at the distal end of the inner cutting blade 9, but to only provide a suction aperture through the distal end of the outer cutting blade 10 at a location that is offset from the longitudinal axis LA. Such a suction aperture would be disposed so as to be covered by and closed by the inner cutting blade 9 when the cutting windows are aligned with each other (the FIG. 4 orientation), but would be uncovered by the distal tip portion of the inner cutting blade 9 when the cutting windows of the inner and outer cutting blades 9 and 10 are misaligned with each other (the FIG. 5 orientation). However, such a structure is disfavored because it is feared that the suction aperture in the outer cutting blade will function to cut tissue when the inner cutting blade is rotating within the outer cutting blade (i.e., during a cutting operation).

The illustrated exemplary embodiments of the surgical tool as set forth above are intended to be illustrative and not limiting. Various changes may be made without departing from the spirit and scope of the invention.

What is claimed is:

1. A surgical instrument comprising:
a first cutting blade having a tubular body with a proximal end and a distal end, a cutting window disposed at a side of the first cutting blade near the distal end;
a second cutting blade having a tubular body with a proximal end and a distal end, a cutting window disposed at a side of the second cutting blade near the distal end, the second cutting blade rotatably disposed inside of the first cutting blade such that the surgical instrument cuts tissue by rotating the second cutting blade within the first cutting blade while a vacuum is applied through an internal bore of the second cutting blade to draw the tissue into the cutting windows of the first and second cutting blades and sever the tissue by rotation of the second cutting blade;
the distal end of the first cutting blade including a first suction aperture through which a longitudinal axis of the first cutting blade extends; and
the distal end of the second cutting blade including a second suction aperture through which a longitudinal axis of the second cutting blade extends,
wherein the surgical instrument can be used as a suction tool by applying the vacuum through the internal bore of the second cutting blade while the second cutting blade is stopped from rotating with the cutting windows of the first and second cutting blades misaligned with each other so that the vacuum is applied through the first and second suction apertures,
wherein an area of the first suction aperture is smaller than an area of the second suction aperture to avoid pinching of tissue between the first suction aperture and the second suction aperture.

2. The surgical instrument of claim 1, wherein the distal end of each of the first and second cutting blades has a spherical shape.

3. The surgical instrument of claim 1, wherein the first and second cutting blades are made from a sterilizable material.

4. The surgical instrument of claim 1, wherein the first and second cutting blades are made from a metal.

5. The surgical instrument of claim 4, wherein the first and second cutting blades are made from stainless steel.

6. The surgical instrument of claim 1, wherein a passage exists between the first and second cutting blades through which a liquid can be supplied.

7. A surgical method comprising:
inserting the surgical instrument of claim 1 into a passage of a patient; and
performing a suctioning operation, the suctioning operation including:
positioning the second cutting blade relative to the first cutting blade so that the cutting windows of the first and second cutting blades are misaligned with each other so that the internal bore of the second cutting blade does not communicate with the passage of the patient through either of the cutting windows of the first and second cutting blades, and
applying a vacuum through the internal bore of the second cutting blade to draw material from the passage of the patient into the internal bore of the second cutting blade through the first and second suction apertures.

8. The surgical method of claim 7, wherein the first and second cutting blades are not rotated relative to each other during the step of applying the vacuum.

9. The surgical method of claim 7, further comprising:
performing a cutting operation either before, after, or both before and after, performing the suctioning operation, wherein the cutting operation includes:
rotating the second cutting blade relative to the first cutting blade while applying the vacuum through the internal bore of the second cutting blade.

10. The surgical method of claim 9, wherein the cutting operation further includes:
supplying liquid through a passage that exists between the first and second cutting blades.

11. A surgical instrument comprising:
an outer cutting blade having a tubular body with a proximal end and an open distal end, a cutting window disposed at a side of the outer cutting blade near the distal end;
an inner cutting blade having a tubular body with a proximal end and a distal end, a cutting window disposed at a side of the inner cutting blade near the distal end, the inner cutting blade rotatably disposed inside of the outer cutting blade such that the surgical instrument cuts tissue by rotating the inner cutting blade within the outer cutting blade while a vacuum is applied through an internal bore of the inner cutting blade to draw the tissue into the cutting windows of the outer and inner cutting blades and sever the tissue by rotation of the inner cutting blade;

the distal end of the inner cutting blade including a suction aperture that remains in fluid communication with the open distal end of the outer cutting blade as the inner cutting blade rotates, wherein the surgical instrument can be used as a suction tool by applying the vacuum through the internal bore of the inner cutting blade while the inner cutting blade is stopped from rotating with the cutting windows of the outer and inner cutting blades misaligned with each other so that the vacuum is applied through the open distal end of the outer cutting blade and the suction aperture of the inner cutting blade, wherein the open distal end of the outer cutting blade is a suction opening, and an area of the suction opening in the outer cutting blade is smaller than an area of the suction aperture in the inner cutting blade to avoid pinching of tissue between the suction opening and the suction aperture.

12. The surgical instrument of claim 11, wherein the suction opening of the outer cutting blade is provided through a distal-most tip of the outer cutting blade.

13. The surgical instrument of claim 11, wherein the distal end of each of the outer and inner cutting blades has a spherical shape.

14. The surgical instrument of claim 11, wherein a longitudinal axis of the inner cutting blade extends through the suction aperture in the inner cutting blade.

15. The surgical instrument of claim 11, wherein a passage exists between the outer and inner cutting blades through which a liquid can be supplied.

16. A surgical method comprising:
inserting the surgical instrument of claim 11 into a passage of a patient; and
performing a suctioning operation, the suctioning operation including:
positioning the inner cutting blade relative to the outer cutting blade so that the cutting windows of the outer and inner cutting blades are misaligned with each other so that the internal bore of the inner cutting blade does not communicate with the passage of the patient through either of the cutting windows of the outer and inner cutting blades, and
applying a vacuum through the internal bore of the inner cutting blade to draw material from the passage of the patient into the internal bore of the inner cutting blade through the suction opening of the outer cutting blade and the suction aperture of the inner cutting blade.

17. The surgical method of claim 16, wherein the outer and inner cutting blades are not rotated relative to each other during the step of applying the vacuum.

18. The surgical method of claim 16, further comprising:
performing a cutting operation either before, after, or both before and after, performing the suctioning operation, wherein the cutting operation includes:
rotating the inner cutting blade relative to the outer cutting blade while applying the vacuum through the internal bore of the inner cutting blade.

19. The surgical method of claim 18, wherein the cutting operation further includes:
supplying liquid through a passage that exists between the outer and inner cutting blades.

20. A surgical instrument comprising:
a first cutting blade having a tubular body with a proximal end and a distal end, a cutting window disposed at a side of the first cutting blade near the distal end;
a second cutting blade having a tubular body with a proximal end and a distal end, a cutting window disposed at a side of the second cutting blade near the distal end, the second cutting blade rotatably disposed inside of the first cutting blade such that the surgical instrument cuts tissue by rotating the second cutting blade within the first cutting blade while a vacuum is applied through an internal bore of the second cutting blade to draw the tissue into the cutting windows of the first and second cutting blades and sever the tissue by rotation of the second cutting blade;
the distal end of the first cutting blade including a first suction aperture; and
the distal end of the second cutting blade including a second suction aperture,
the first and second suction apertures being aligned with each other such that an open suction passage exists between the internal bore and an area external of the surgical instrument through the first and second suction apertures while the second cutting blade does not rotate and while the second cutting blade rotates within the first cutting blade, whereby the surgical instrument can be used as a suction tool by applying the vacuum through the internal bore of the second cutting blade while the second cutting blade is stopped from rotating with the cutting windows of the first and second cutting blades misaligned with each other so that the vacuum is applied through the open suction passage,
wherein an area of the first suction aperture is smaller than an area of the second suction aperture to avoid pinching of tissue between the first suction aperture and the second suction aperture.

21. The surgical instrument of claim 20, wherein the distal end of each of the first and second cutting blades has a spherical shape.

22. The surgical instrument of claim 20, wherein a passage exists between the first and second cutting blades through which a liquid can be supplied.

23. A surgical method comprising:
inserting the surgical instrument of claim 20 into a passage of a patient; and
performing a suctioning operation, the suctioning operation including:
positioning the second cutting blade relative to the first cutting blade so that the cutting windows of the first and second cutting blades are misaligned with each other so that the internal bore of the second cutting blade does not communicate with the passage of the patient through either of the cutting windows of the first and second cutting blades, and
applying a vacuum through the internal bore of the second cutting blade to draw material from the passage of the patient into the internal bore of the second cutting blade through the open suction passage.

24. The surgical method of claim 23, wherein the first and second cutting blades are not rotated relative to each other during the step of applying the vacuum.

25. The surgical method of claim 23, further comprising:
performing a cutting operation either before, after, or both before and after, performing the suctioning operation, wherein the cutting operation includes:
rotating the second cutting blade relative to the first cutting blade while applying the vacuum through the internal bore of the second cutting blade.

26. The surgical method of claim 25, wherein the cutting operation further includes:

supplying liquid through a passage that exists between the first and second cutting blades.

* * * * *